US009879299B2

(12) United States Patent
Yamakawa et al.

(10) Patent No.: US 9,879,299 B2
(45) Date of Patent: Jan. 30, 2018

(54) METHOD FOR MONITORING AND CONTROLLING CELLULAR GROWTH

(71) Applicant: Hewlett-Packard Development Company, L.P., Houston, TX (US)

(72) Inventors: Mineo Yamakawa, Palo Alto, CA (US); Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 254 days.

(21) Appl. No.: 14/475,532

(22) Filed: Sep. 2, 2014

(65) Prior Publication Data

US 2014/0370493 A1 Dec. 18, 2014

Related U.S. Application Data

(62) Division of application No. 13/754,860, filed on Jan. 30, 2013, now abandoned.

(51) Int. Cl.
| | | |
|---|---|---|
| *C12Q 3/00* | (2006.01) | |
| *C12Q 1/02* | (2006.01) | |
| *C12M 1/34* | (2006.01) | |
| *G01N 33/483* | (2006.01) | |

(52) U.S. Cl.
CPC ............... *C12Q 1/02* (2013.01); *C12M 41/36* (2013.01); *C12M 41/46* (2013.01); *C12Q 3/00* (2013.01); *G01N 33/4833* (2013.01)

(58) Field of Classification Search
None
See application file for complete search history.

(56) References Cited

U.S. PATENT DOCUMENTS

| | | |
|---|---|---|
| 7,388,200 B2 | 6/2008 | Stewart et al. |
| 8,048,377 B1 | 11/2011 | Zhou et al. |
| 2007/0282247 A1 | 12/2007 | Desai et al. |

(Continued)

FOREIGN PATENT DOCUMENTS

| | | |
|---|---|---|
| WO | WO-2011133143 | 10/2011 |
| WO | WO-2011133144 | 10/2011 |

(Continued)

OTHER PUBLICATIONS

Aksoy et al., Role of Vibrational Spectroscopy in Stem Cell Research, Spectroscopy: An International Journal, vol. 27, 2012, Issue 3, pp. 167-184.

(Continued)

*Primary Examiner* — Rebecca L Martinez
(74) *Attorney, Agent, or Firm* — Thorpe, North & Western L.L.P.

(57) ABSTRACT

The present disclosure is drawn to a device for monitoring and controlling live cells and associated methods. In an example, the device can include a plurality of elongated nanostructures affixed to a substrate. The elongated nanostructures can each have an attachment end and a free end opposite the attachment end. The free end includes a metal and the attachment end is affixed to the substrate. The device can further include a functionalization layer that is coated on the free end of at least a portion of the plurality of elongated nanostructures. The functionalization layer can be formulated to retain live cells, and the device can be configured to be used in conjunction with a detector, such as a Raman spectrometer, in order to monitor growth of live cells.

23 Claims, 5 Drawing Sheets

(56) References Cited

U.S. PATENT DOCUMENTS

| | | |
|---|---|---|
| 2008/0118432 A1 | 5/2008 | Bergstein et al. |
| 2010/0273258 A1 | 10/2010 | Lannutti et al. |
| 2011/0188034 A1 | 8/2011 | Stuke et al. |
| 2011/0293666 A1 | 12/2011 | Wang et al. |

FOREIGN PATENT DOCUMENTS

| | | |
|---|---|---|
| WO | WO-2012054024 | 4/2012 |
| WO | WO-2012059748 | 5/2012 |

OTHER PUBLICATIONS

Bucaro et al., Fine-Tuning the Degree of Stem Cell Polarization and Aligment on Ordered Arrays of High-Aspect-Ratio Nanopillars, ACSNANO, vol. 6, No. 7, 2012, pp. 6222-6230.

Dolatshahi-Pirouz et al., Micro- and Nanoengineering Approaches to Control Stem Cell-Biomaterial Interactions, J. Funct. Biomater., 2011, 2, pp. 88-106.

Downes, A. et al., Optical Spectroscopy for Nonivasive Monitoring of Stem Cell Differentiation, (Web Page), Journal of Biomedicine and Biotechnology, Nov. 11, 2009, vol. 2010.

El-Said et al., Analysis of Intracellular State Based on Controlled 3D Nanostructures Mediated Surface Enhanced Raman Scattering, PLOS ONE, vol. 6, Issue 2, Feb. 2011.

Hu et al., Gold Nanofingers for Molecule Trapping and Detection, J. Am. Chem. Soc., 2010, 132, pp. 12820-12822.

Huh et al., From 3D cell culture to organs-on-chips, Trends in Cell Biology, Dec. 2011, vol. 21, No. 12, pp. 745-754.

Moody et al., In Situ Monitoring of Adipogenesis with Humban-Adipose-Derived Stem Cells Using Surface-Enhanced Raman Spectroscopy, Applied Spectroscopy, vol. 64, No. 11, 2010, pp. 1227-1233.

Ou et al., Hot-Spot Engineering in Polygonal Nanofinger Assemblies for Surface Enhanced Raman Spectroscopy, ACS Publications/Nano Letters, 2011 American Chemical Society, pp. 2538-2542.

Placzek et al., Stem cell bioprocessing: fundamentals and principles, J. R. Soc. Interface, 2009, 6, pp. 209-232.

Rodrigues et al., Stem cell cultivation in bioreactors, Biotechnology Advances 29, 2011, pp. 815-829.

Sathuluri et al., Gold Nanoparticle-Based Surface-Enhanced Raman Scattering for Noninvasive Molecular Probing of Embryonic Stem Cell Differentiation, PLOS ONE, vol. 6, Issue 8, Aug. 2011.

Wittig et al., Preparation of Cells Cultured on Silicon Wafers for Mass Spectrometry Analysis, Microscopy Research and Technique 66:248-258 (2005).

Yang et al., Assaying stem cell mechanobiology on microfabricated elastomeric substrates with geometrically modulated rigidity, Nature Protocols, vol. 6, No. 2, 2011, pp. 187-213.

Bagnaninchi, P.O. et al., Real-time Label-free Monitoring of Adipose-derived Stem Cell Differentiation with Electric Cell-substrate Impedance Sensing, (Research Paper), Proceedings of the National Academy of Science, Apr. 19, 2011, pp. 6462-6467, vol. 108, No. 16.

METHOD FOR MONITORING AND CONTROLLING CELLULAR GROWTH

CROSS-REFERENCE TO RELATED APPLICATION

The present application is a divisional of co-pending U.S. patent application Ser. No. 13/754,860 filed on Jan. 30, 2013, the full disclosure of which is hereby incorporated by reference.

BACKGROUND

Generally the successful bioprocessing of cells, such as stem cells, relies on robust and reproducible culture conditions and processes. For example, both in vivo and in vitro, differentiation and self-renewal of stem cells or pluripotent cells may be dominated by signals from their surrounding microenvironment. Identification of purity and differentiation stages of stem cells can be one of the greatest challenges of stem cell biology and regenerative medicine. The existing methods to carefully monitor and characterize cells have some unwanted effects on the properties of stem cells, and these methods also do not provide real-time information about cellular conditions. For example, standard biological assays to analyze stem cells often involve fixation, staining, and/or drying steps that destroy cellular characteristics, and cannot provide real time information about natural life process of the cells. Thus, improvements in these and other areas would be an advancement in the art.

BRIEF DESCRIPTION OF THE DRAWINGS

Additional features and advantages of the disclosure will be apparent from the detailed description which follows, taken in conjunction with the accompanying drawings, which together illustrate, by way of example, features of the disclosure.

Reference will now be made to the exemplary embodiments illustrated, and specific language will be used herein to describe the same. It will nevertheless be understood that no limitation of the scope of the invention is thereby intended.

DETAILED DESCRIPTION

Before the present disclosure is set forth described, it is to be understood that this disclosure is not limited to the particular process steps and materials disclosed herein because such process steps and materials may vary somewhat. It is also to be understood that the terminology used herein is used for the purpose of describing particular embodiments only. The terms are not intended to be limiting because the scope of the present disclosure is intended to be limited only by the appended claims and equivalents thereof.

It has been recognized that it would be advantageous to develop device or system for monitoring and controlling cellular growth utilizing a new type of surface-enhanced Raman spectroscopy (SERS) structures. For example, the success of stem cell bioprocessing relies on robust reproducible culture conditions and processes. In vivo, differentiation and self-renewal of stem cells are dominated by signals from their surrounding microenvironment. This microenvironment is composed of other cell types as well as numerous chemical, mechanical, and topographical cues at the micro- and nano-scale, which collectively control the cell behavior. Many techniques for monitoring cells, such as stem cells, often have had unwanted effects on the cells and are not able to provide real-time information about the cellular conditions. The devices and methods of the present disclosure are able to provide real-time monitoring of cells without the use of nanoparticles, such as SERS active materials, e.g., metal particles, which in turn allows for enhanced control of cellular growth and differentiation.

With the above in mind, the present disclosure sets forth devices and related methods that utilize a plurality of elongated nanostructures affixed to a substrate with a functionalization layer that is coated on the nanostructures. The functionalization layer can be formulated to retain live cells, and a detector, such as a Raman spectrometer, can be used to monitor the cells. It is noted that when discussing a device for monitoring and controlling cellular growth, a method of growing live cells, or a method of making a device for monitoring and controlling cellular growth, each of these discussions can be considered applicable to the other embodiment, whether or not they are explicitly discussed in the context of that embodiment. Thus, for example, in discussing an elongated nanostructure for a device for monitoring and controlling cellular growth, such an elongated nanostructure ligand can also be used in a method of growing live cells, and vice versa.

With this in mind, a device for monitoring and controlling cellular growth is provided. The device includes a substrate, a plurality of elongated nanostructures, and a functionalization layer. The plurality of elongated nanostructures can include an attachment end and a free end opposite the attachment end, the free end including a Metal and the attachment end affixed to the substrate. The functionalization layer can be coated on the free end of at least a portion of the plurality of elongated nanostructures, and can be formulated to retain live cells. By "retain" live cells, this term includes both maintaining the health of live cells as well as growing a cell culture. The device can also be configured to be used in conjunction with a detector, externally located or integrated as a part of the device, in order to monitor growth of live cells.

With specific reference to the nanostructures described herein, the term "nanostructure(s)" refers to any structure having dimensions of width or diameter less than 1 micron. As such, an elongated nanostructure can include structures that have an aspect ratio with a length at least two times longer than the shortest width. Examples can include nanocones, nanopyramids, nanorods, nanobars, nanofingers, nanopoles, nanograss, etc. In one example, the nanostructure can be a metallic capped nanofinger. As used herein, the terms "nanocones," "nanopyramids," "nanorods," "nanobars," "nanopoles" and "nanograss," refer to structures that are substantially: conical, pyramidal, rod-like, bar-like, pole-like and grass-like, respectively, which have nano-dimensions as small as a few tens of nanometers (nm) in height and a few nanometers in diameter, or width. For example, flexible columns may include nano-columns (or other elongated nanostructure) having the following dimensions: a diameter (or width) of 10 nm to 500 nm, a height of 20 nm to 2 micrometers (µm), and a gap between flexible columns of 20 nm to 500 nm. The terms of art, "substantially conical," "substantially pyramidal," "substantially rod-like," "substantially bar-like," "substantially pole-like" and "substantially grass-like," refers to structures that have nearly the respective shapes of cones, pyramids, rods, bars, poles and grass-like asperities within the limits of fabrication in the nanotechnology arts.

Generally, the elongated nanostructure(s) described herein can include a non-metallic column with a metallic coating or metallic cap. In one example, the nanostructure can include a polymer, such as a resist, coated with a SERS active material or metal, such as gold, silver, copper, platinum, aluminum, etc., or the combination of those metals in the form of alloys. Generally, the SERS active metal can be selectively coated on the tips of the non-metallic column or deposited thereon. In addition, the SERS active metal can be a multilayer structure, for example, 10 to 100 nm silver layer with 1 to 50 nm gold over-coating, or vice versa. Additionally, the SERS active metal can be further coated with a thin dielectric layer.

Generally, the use of a polymer can render the nanostructures sufficiently flexible to permit bending so that the tips meet at the top of the structure. Examples of suitable polymers include, but are not limited to, polymethyl methacrylate (PMMA), polycarbonate, siloxane, polydimethylsiloxane (PDMS), photoresist, nanoimprint resist, and other thermoplastic polymers and UV curable materials including one or more monomers/oligomers/polymers. In another example, the nanostructures can include an inorganic material having sufficient flexibility to bend. Examples of such inorganic materials include silicon oxide, silicon, silicon nitride, alumina, diamond, diamond-like carbon, aluminum, copper, and the like.

As discussed, the nanostructures can include a metallic cap, which can be in the form of nanospheres, prolate nanoellipsoids, oblate nanoellipsoids, nanodisks, nanoplates, etc., for example, having a width or diameter of 500 nm or less and which are associated with or attached to an elongated nanostructure. In one example, the metallic cap may possess shape-induced magnetic anisotropy. As used herein, the terms "nanospheres," "prolate nanoellipsoids," "oblate nanoellipsoids," "nanodisks," and "nanoplates," refer to structures that are substantially: spherical, prolate ellipsoidal, oblate ellipsoidal, disk-like, and plate-like, respectively, which have nano-dimensions as small as a few nanometers in size: height, diameter, or width. In addition, the terms "substantially spherical," "substantially prolate ellipsoidal," "substantially oblate ellipsoidal," "substantially disk-like," and "substantially and plate-like," refers to structures that have nearly the respective shapes of spheres, prolate ellipsoids, oblate ellipsoids, disks, and plates within the limits of fabrication with nanotechnology.

The devices for monitoring and controlling cellular growth disclosed herein can further include a functionalization layer. The functionalization layer can be coated or deposited or adsorbed via SAMs (self-assembled monolayers) on the free end of each of the plurality of the elongated nanostructures and/or on substrate. SAMs can provide a variety of surface functional groups such as hydroxyl (OH), carboxyl (COOH), amine ($NH_2$), methyl ($CH_3$), etc. Generally, the functionalization layer can be formulated to retain live cells as well as allow the cells to be cultured and thrive.

In one example, the functionalization layer can include a peptide functionalized polymer. Non-limiting examples of peptides that can be functionalized on the polymer can include the peptide with specific amino acid sequence motifs such as arginine-glycine-aspartic acid (RGD), arginine-glycine-aspartic acid-serine (RGD+), glycine-arginine-glycine-aspartic acid-serine (GRGDS), etc., or combinations thereof. In another aspect, the functionalization layer can include proteins such as fibronectin, fibrin, laminin, collagen, elastin, or vitronection.

In monitoring cellular cultures, the devices described herein can be adapted for use with various electronic monitoring or controlling apparatuses. For example, a detector can be used, such as one or more selected from the group of a colorimeter, a reflectometer, a spectrometer, a spectrophotometer, a Raman spectrometer, and an optical microscope. With specific regard to the use of a Raman spectrometer, the technique of Surface-enhanced Raman spectroscopy (SERS) can be implemented, which is a spectroscopic technique used in condensed matter physics and chemistry to study molecular systems. However, this technique can be likewise used to monitor live cellular cultures as well as described herein.

In general, Raman spectroscopy can be used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation photons. The Raman spectrum of different molecules or matters has characteristic peaks that can be used to identify the species. As such, Raman spectroscopy can likewise be a useful technique for chemical or bio-logical sensing applications, such as monitoring cellular cultures in accordance with examples of the present disclosure.

Figure 1A:
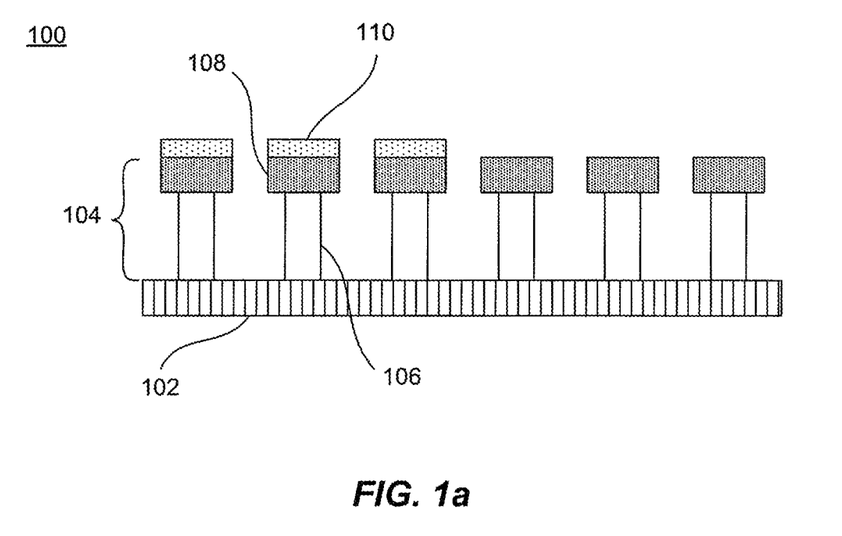
FIGS. 1a and 1b are a cross-sectional views of live cell monitoring and controlling devices in accordance with examples of the present disclosure.
Figure 1B:
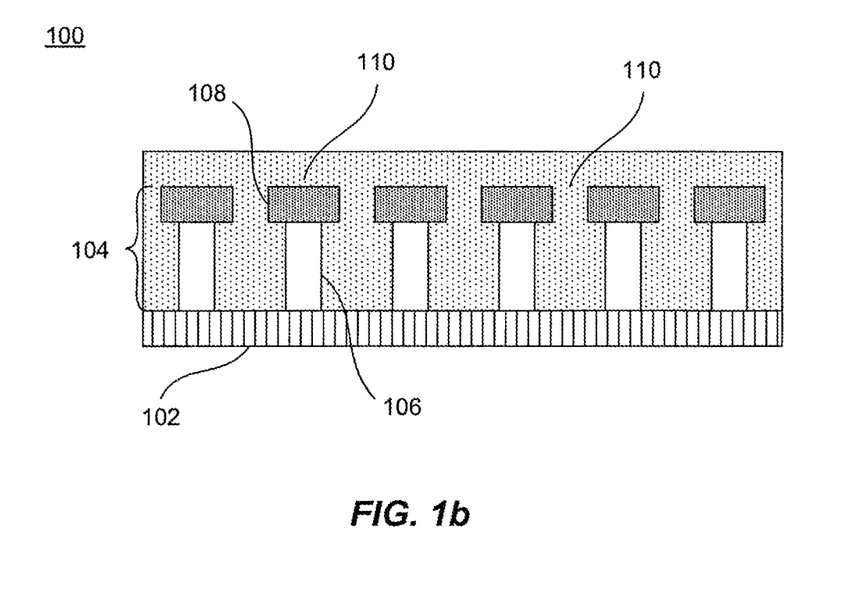

Referring to FIGS. 1a and 1b, a device 100 for monitoring and controlling live cells can include a substrate 102 having an elongated nanostructure 104 attached thereto. The elongated nanostructure has a columnar structure 106 with a metallic cap 108 deposited thereon. Further, a functionalization layer 110 is disposed on all or a portion of the elongated nanostructures or a portion of the substrate. As shown in FIG. 1a, the functionalization layer can coat or substantially coat the tops of the nanostructures. However, in some aspects, such as shown in FIG. 1b, the functionalization layer may cover other portions of the nanostructures including all or portions of the columnar structure. It is noted that in subsequent FIGS., the functionalization layer is shown as being disposed on a top of the nanostructures, but it is to be understood that this is done for convenience, as the coatings can likewise be applied to the device as shown in FIG. 1b as well.

Figure 2:
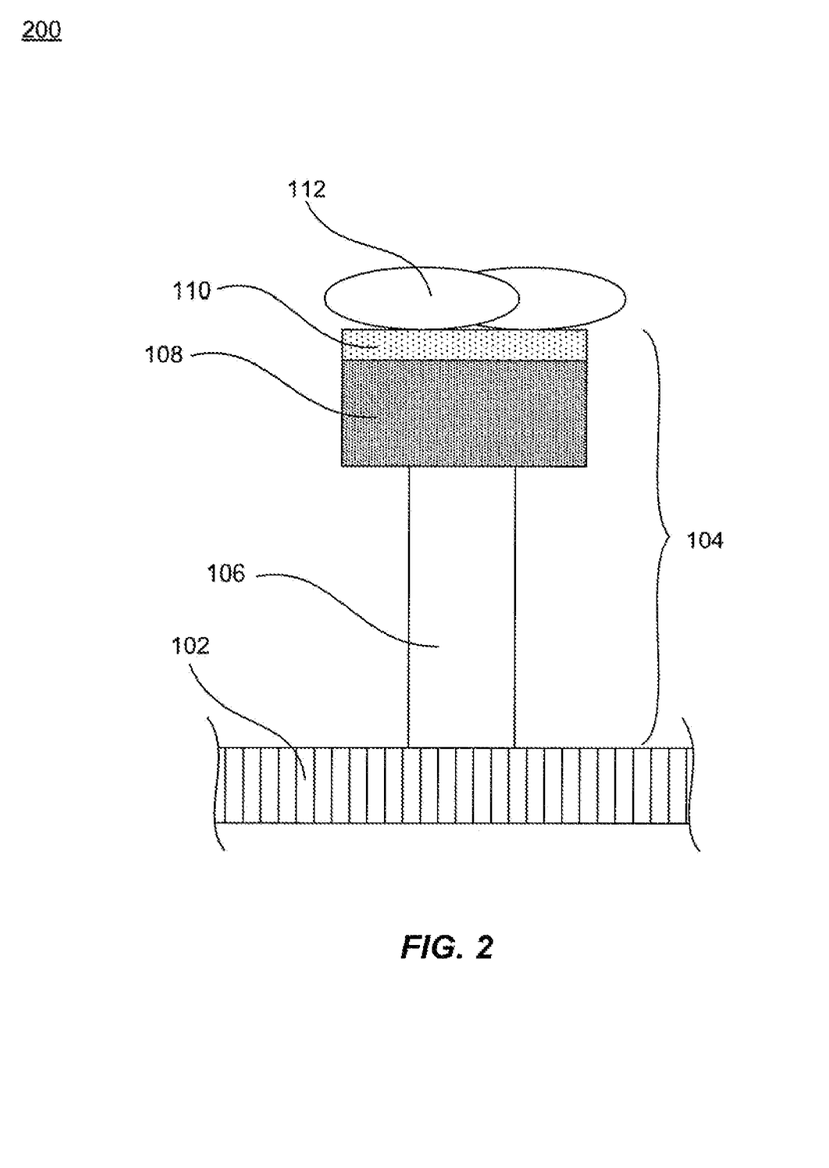
FIG. 2 is another cross-sectional view of a live cell monitoring and controlling device in accordance with an example of the present disclosure.

Referring to FIG. 2, an expanded view of a single elongated nanostructure 104 having live cells 112 disposed in or on the functionalization layer 110 of the nanostructure is shown. When the functionalization extends to cover other portion of the structure, live cells can be placed, or extended to, other areas. Typical cells might span over several nanostructures and/or extend into other areas such as 106, 108, and 102. It is noted that the elements of FIG. 2 are not necessarily drawn to scale, nor does it represent every live cell monitoring and controlling device available for use herein, i.e. it provides merely an example of one such sensing device having live cells disposed thereon. In further detail in this example, similar to FIGS. 1a and 1b, the monitoring and controlling device 200 can also include a substrate 102, and columnar structure 106 with a metallic cap 108 deposited thereon with the functionalized layer disposed on at least a portion of the elongated nanostructure.

Figure 3:
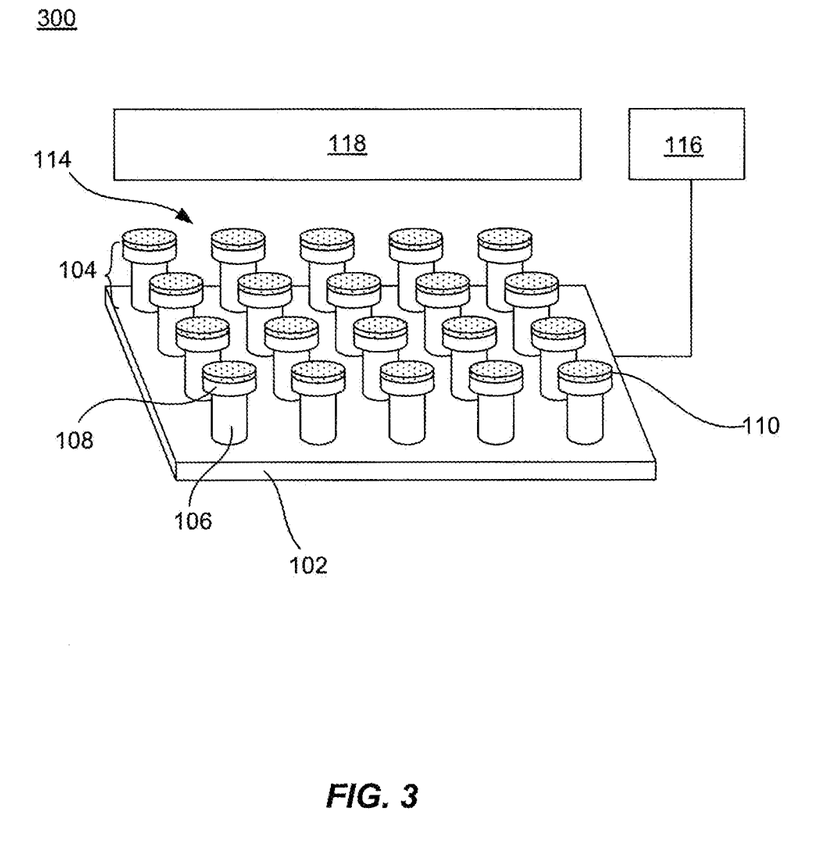
FIG. 3 is a perspective view of a live cell monitoring and controlling device in accordance with an example of the present disclosure.

Referring to FIG. 3, a device for monitoring and controlling live cells 300 can include a substrate 102 having an array 114 of elongated nanostructures 104 attached thereto. The elongated nanostructures can include columnar structures 106 with a metallic caps 108 deposited thereon. A functionalized layer 110 can be disposed on all or a portion of the elongated structures and/or the substrate. The monitoring and controlling device can further be associated with a detector 116 operatively coupled to the nanostructures, which in some aspects can form a part of the device. The detector, or a combination of detectors, can be any of a variety of devices that would be functional in monitoring and or controlling live cell growth in accordance with examples of the present disclosure. Examples of suitable devices can include colorimeters, reflectometers, spectrometers, spectrophotometers, Raman spectrometers, optical microscopes, instruments for measuring luminescence, or the like. Additionally, a source of excitation energy 118, such as a light source or a laser source, is also shown.

Thus, devices of the present disclosure can be configured to be used in conjunction with a detector in order to monitor growth of lives cells. In one aspect, the device can include a plurality of live cells disposed in the functionalization layer. Generally, any type of live cells can be monitored and controlled utilizing the devices and methods of the present disclosure. On example of cell types that can be monitored and controlled include stem cells, such as stem cells from a mammal.

Figure 4:
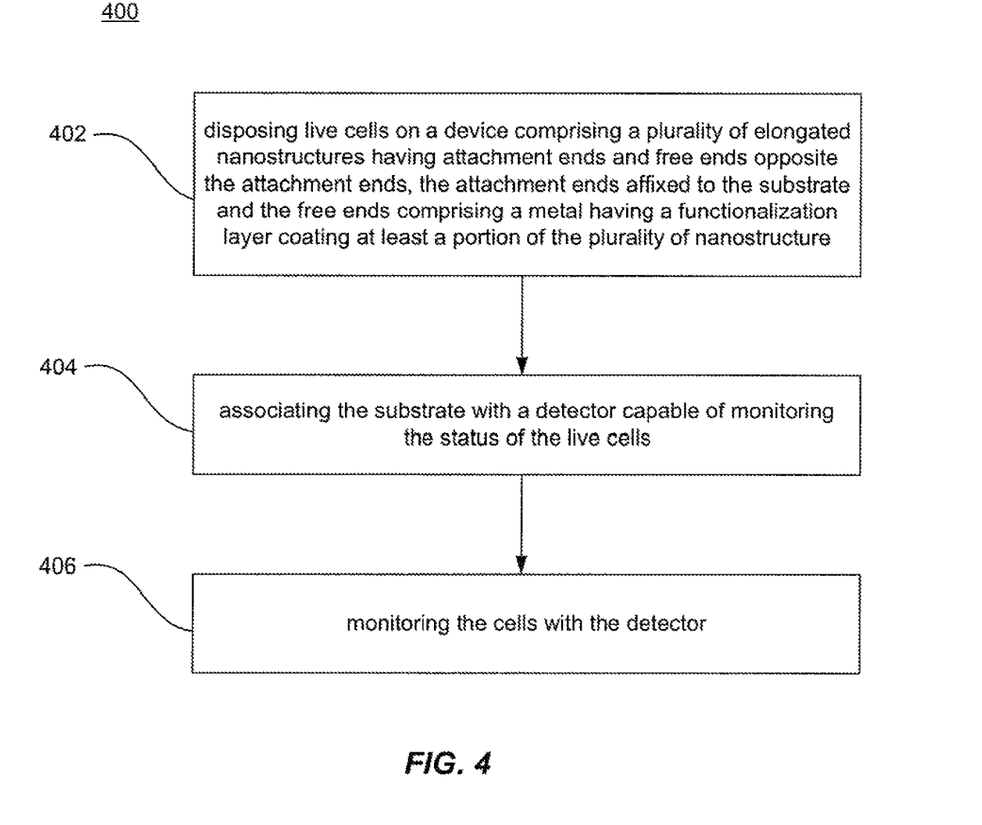
FIG. 4 is a flow chart of a method in accordance with an example of the present disclosure.

As mentioned, the devices of the present disclosure can be used in order to grow live cells. Thus, these devices, or other similar devices, can be used in accordance with various methods of the present disclosure. As shown in FIG. 4, a method 400 of growing live cells is provided in which lives cells can be disposed 402 on one of the devices disclosed herein. For example, in one aspect, the device can have a plurality of elongated nanostructures having attachment ends and free ends opposite the attachment ends. The attachment ends can be affixed to the substrate and the free ends can have metal cap and at least a portion of the free ends can have a functionalization layer coated thereon. The substrate having cells disposed thereon can be associated 404 with a detector that is capable of monitoring the status of the live cells. The live cells can likewise be monitored 406 utilizing the detector. Any of the detectors set forth above can be utilized. In one aspect, the detector can be a Raman spectrometer.

The method can further include a step of influencing or controlling cell growth based on information received during monitoring. The ability to control or influence the cell growth and/or differentiation of the cells can be correlated to the ability of the devices of the present disclosure to provide real-time or substantially real-time monitoring of the state of the cells and the conditions of the medium (e.g. functionalization layer) in which the cells are being cultured. Because the functionalization layer is disposed on the elongated nanostructures with metallic caps, certain scanning mechanisms i.e. detectors, such as a Raman spectrometer, can be utilized more effectively due to the surface enhancement provided by the metallic capped nanostructures. This increased effectiveness in turn provides for more accurate information regarding the state of the cells and the surround medium to be detected.

Once the status and/or condition of the cells and their surround growth medium are detected, influencing or controlling of the cell growth can be accomplished by any known technique in the art. For example, in one aspect, cell growth or differentiation can be controlled or influenced by the addition or removal of certain chemical or biological reagents or physical, mechanical, topographic stimuli and forces/stress.

Figure 5:
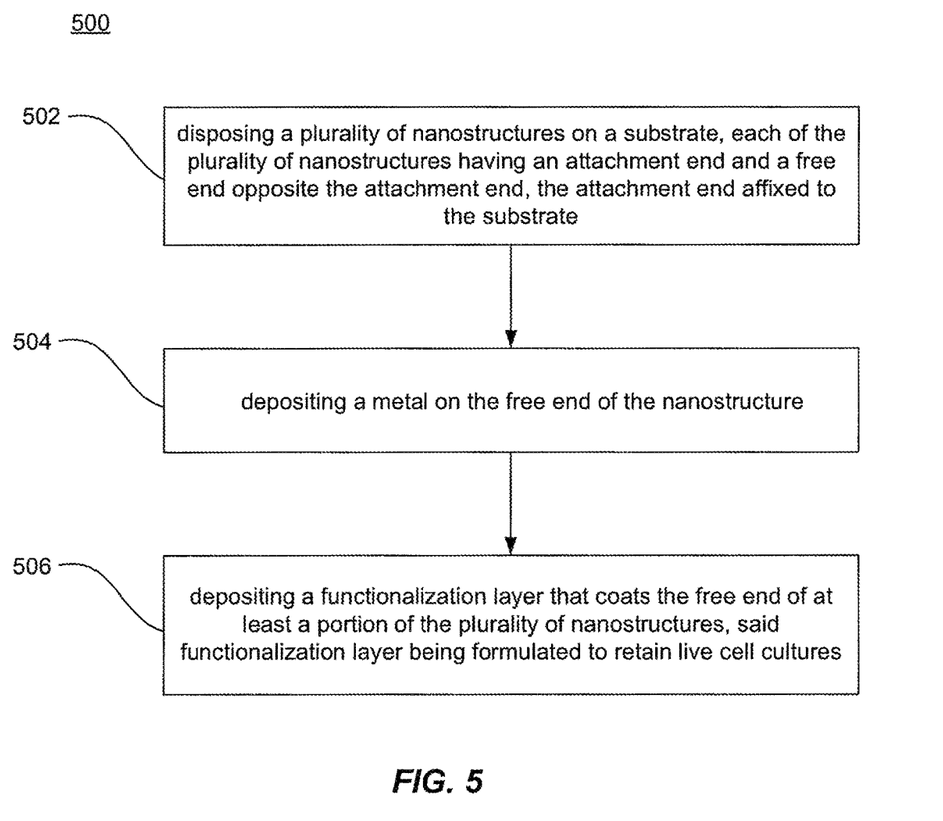
FIG. 5 is a flow chart of another method in accordance with an example of the present disclosure.

In another example, a method 500 for making a device for monitoring cellular growth is also provided, as shown in FIG. 5. The method includes attaching 502 a plurality of nanostructures to a substrate, each of the plurality of nanostructures having an attachment end and a free end opposite the attachment end, the attachment end affixed to the substrate. A metal can be deposited 504 on the free end of the nanostructure and a functionalization layer can be deposited 506 on at least a portion of the plurality of the nanostructures the functionalization layer being formulated to retain live cell cultures.

It is be noted that, as used in this specification and the appended claims, the singular forms "a," "an," and "the" include plural referents unless the context clearly dictates otherwise.

As used herein, a plurality of steps, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. Additionally, a numerical range with a lower end of "0" can include a sub-range using "0.1" as the lower end point.

EXAMPLES

The following illustrates some examples of the present devices and methods. However, it is to be understood that the following are only exemplary or illustrative of the application of the principles of the present disclosure. Numerous modifications, alternatives, and methods may be devised by those skilled in the art without departing from the spirit and scope of the present compositions and methods. The appended claims are intended to cover such modifications and arrangements. Thus, while the present devices and methods have been described above with particularity, the following examples provide further detail in connection with what are presently deemed to be acceptable embodiments.

Example 1—Preparation of Gold Elongated Nanostructure with Functionalization Layer Deposited Thereon A general example of the present disclosure for preparing a live cell monitoring and controlling device is as follows. In brief, a plurality of nanostructure, in particularly, the nanofinger structure can be made through nanoimprinting or roll-to-roll process on a substrate, such as plastic, glass, or polymer material. The nanostructures are subsequently coated at the tip with a gold metallic material by e-beam evaporation. A functionalization layer of arginine-glycine-aspartic acid (RGD), or arginine-glycine-aspartic acid-serine (RGD+), or glycine-arginine-glycine-aspartic acid-serine (GRGDS), etc., is deposited on the surfaces of the upper surfaces of the nanostructures at a thickness of about less than 10 nm.

Example 2—Monitoring of Live Cells Utilizing SERS

A device for monitoring and controlling live cells is prepared, such as described in Example 1. Live cells are deposited on the functionalization layer of the devices nanostructures. The device is associated with a Raman Spectrometer and the cells are monitored by repeated scanning the device with the Raman Spectrometer. The nanostructured SERS substrate provides SERS enhanced monitoring of the live cells with Raman spectroscopy, and can also provide more optimal culture environments. The real-time or near real-time monitoring of the live cells with SERS enhanced Raman spectroscopy provides a feedback of a variety of (bio)chemical information and states of the live cells useful for controlling and optimizing the culture conditions. For example, SERS spectroscopic profiles and their changes can monitor the states of a variety of bio-components in the cells such as lipids for C—O or C—C phosphate stretching, $CH_2$ and $CH_3$ deformation or bending, lipid vibrations, proteins for cysteine disulfide bond, C—C twist or stretch, ring breathing, C—N stretch or bend, C—H bend, $CH_3$ rocking, amide vibration, protein vibration, nucleotides for asymmetric phosphate stretch in DNA backbone, etc. The measured results in turn provide the potential for beneficial changes in physicochemical variables of cultures such as pH, dissolved oxygen, osmolarity, temperature as well as biochemical control of the levels of key nutrients and metabolites, and growth factors based on the established and published or experimental protocols. If the outcome of such a change does not appear to be beneficial, the changes can be immediately reverted and/or alternative changes can be re-selected. The process of monitoring-optimizing for cell cultures in real-time can be repeated until desired results are obtained. Repeated scanning allows for active monitoring of the cells as they live or differentiate in the functionalization layer.

While the disclosure has been described with reference to certain examples, those skilled in the art will appreciate that various modifications, changes, omissions, and substitutions can be made without departing from the spirit of the disclosure. It is intended, therefore, that the present disclosure be limited only by the scope of the following claims.

What is claimed is:

1. A method of growing live cells, comprising:
disposing live cells on a device comprising a plurality of elongated nanostructures having attachment ends and free ends opposite the attachment ends, the attachment ends affixed to a substrate and the free ends comprising a metal and a functionalization layer coating the free end of at least a portion of the plurality of nanostructures;
associating the substrate with a detector capable of monitoring the status of the live cells;
monitoring the cells with the detector; and
influencing or controlling cell growth based on information received from the detector during monitoring.

2. The method of claim 1, wherein the detector is selected from the group of a colorimeter, a reflectometer, a spectrometer, a spectrophotometer, a Raman spectrometer, and an instrument for measuring luminescence.

3. The method of claim 1, wherein the functionalization layer includes a peptide functionalized polymer selected from the group of arginine-glycine-aspartic acid, arginine-glycine-aspartic acid-serine, glycine-arginine-glycine-aspartic acid-serine, or combinations thereof.

4. The method of claim 1, wherein the plurality of elongated nanostructures include columnar structures that are less conductive than the metal.

5. The method of claim 1, wherein the metal is selected from the group of gold, silver, copper, aluminum, platinum, and combinations thereof.

6. The method of claim 1, wherein the functionalization layer includes at least one of a peptide functionalized polymer, a fibronectin, fibrin, laminin, collagen, elastin, and vitronection.

7. The method of claim 1, wherein the live cells are disposed in the functionalization layer.

8. The method of claim 1, wherein the live cells are stem cells.

9. The method of claim 1, wherein the substrate is in the form of a dish.

10. The method of claim 1, wherein the metal comprises a multilayer structure comprising:
a first layer of the first metal, the first layer having a thickness of 10 nm to 100 nm; and
a second layer of the second metal, the second layer having a thickness of 1 nm to 50 nm.

11. The method of claim 9, wherein the second layer overlies the first layer.

12. The method of claim 1, wherein each of the plurality of elongated nanostructures comprise:
a columnar structure having a first diameter and being less conductive than the metal; and
a metallic cap of the metal on a tip of the columnar structure, the cap having second diameter greater than the first diameter.

13. The method of claim 1, wherein the plurality of elongated nanostructures are sufficiently flexible to permit bending such that tips of the nanostructures meet at the free end of each of the nanostructures.

14. The method of claim 1, wherein the plurality of elongated nanostructures are submersed in the functionalization layer.

15. The method of claim 1, wherein the plurality of elongated nanostructures are spaced apart along a surface of the substrate by a gap of 20 nm to 500 nm.

16. The method of claim 1, wherein the detector comprises a Raman spectrometer.

17. A method of growing live cells, comprising:
disposing live cells on a device comprising a plurality of elongated nanostructures having attachment ends and free ends opposite the attachment ends, the attachment ends affixed to a substrate and the free ends comprising a metal and a functionalization layer coating the free end of at least a portion of the plurality of nanostructures, wherein the plurality of elongated nanostructures are sufficiently flexible to permit bending such that tips of the nanostructures meet at the free end of each of the nanostructures;
associating the substrate with a detector capable of monitoring the status of the live cells; and
monitoring a characteristic of the live cells, other than population of the cells, with the detector.

18. A method of growing live cells, comprising:
disposing live cells on a device comprising a plurality of elongated nanostructures having attachment ends and free ends opposite the attachment ends, the attachment ends affixed to a substrate and the free ends comprising a metal and a functionalization layer coating the free end of at least a portion of the plurality of nanostructures;
associating the substrate with a detector capable of monitoring the status of the live cells; and
repeatedly detecting and measuring a characteristic of the live cells, other than population of the live cells, with the detector at spaced time intervals as the live cells live on the device.

19. The method of claim 18, wherein the repeated detecting and measuring of a characteristic of the live cells comprises:
detecting and measuring the characteristic of the live cells with the detector at a first time as the live cells live on the device; and
detecting and measuring the characteristic of the live cells with the detector at a second time, spaced from the first time as the live cells live on the device,
wherein the method further comprises altering a physiochemical variable of a culture of the live cells at a third time between the first time and the second time based upon the detected and measured characteristic of the live cells.

20. The method of claim 1, wherein the influencing or controlling of cell growth that is based upon information received from the detector during monitoring is an action selected from a group of actions consisting of: adding chemical reagents to a culture of the live cells; removing chemical reagents to the culture of the live cells; adding chemicals to the culture of the live cells; removing chemicals from the culture of the live cells, applying a physical, mechanical, topographic stimulus to the culture of the live cells or applying forces/stress to the culture of the live cells.

21. The method of claim 1, wherein the influencing or controlling of cell growth that is based upon information received from the detector during monitoring comprises altering a characteristic of the culture of the cells, the characteristic that is altered being selected from a group of characteristics consisting of: pH, dissolved oxygen, osmolarity, temperature, nutrient level, metabolites level and growth factors.

22. The method of claim 1, wherein the detector comprises a surface enhanced Ramen spectroscopy sensor and wherein the information received from the detector comprises a state of a bio-component of the cells.

23. The method of claim 22, wherein the state of the bio-component of the cells is selected from a group of bio component states consisting of: lipids for C—O or C—C phosphate stretching, CH2 and CH3 deformation or bending, lipid vibrations, proteins for cysteine disulfide bond, C—C twist or stretch, ring breathing, C—N stretch or bend, C—H bend, CH3 rocking, amide vibration, protein vibration, and nucleotides for asymmetric phosphate stretch in DNA backbone.

* * * * *

UNITED STATES PATENT AND TRADEMARK OFFICE
CERTIFICATE OF CORRECTION

PATENT NO. : 9,879,299 B2  Page 1 of 1
APPLICATION NO. : 14/475532
DATED : January 30, 2018
INVENTOR(S) : Mineo Yamakawa et al.

It is certified that error appears in the above-identified patent and that said Letters Patent is hereby corrected as shown below:

In Column 10, Line 31, in Claim 23, delete "CH2 and CH3" and insert -- $CH_2$ and $CH_3$ --, therefor.

In Column 10, Line 34, in Claim 23, delete "CH3" and insert -- $CH_3$ --, therefor.

Signed and Sealed this
Nineteenth Day of June, 2018

Andrei Iancu
*Director of the United States Patent and Trademark Office*